United States Patent [19]

Huttunen et al.

[11] 4,304,995
[45] Dec. 8, 1981

[54] METHOD AND APPARATUS FOR MEASURING THE WALL THICKNESS IN A PLASTIC ARTICLE

[75] Inventors: Paavo Huttunen; Matti Otala; Jarmo Karvonen; Martti Karppinen, all of Oulu; Esko Sohlo, Espoo, all of Finland

[73] Assignee: Oy Kolster AB, Helsingfors, Finland

[21] Appl. No.: 73,242

[22] Filed: Sep. 6, 1979

[30] Foreign Application Priority Data

Sep. 11, 1978 [FI] Finland .................................. 782773

[51] Int. Cl.³ .............................................. G01J 1/00
[52] U.S. Cl. .............................. 250/339; 250/223 B; 250/341
[58] Field of Search ........... 250/252, 339, 341, 223 B, 250/349, 353

[56] References Cited

U.S. PATENT DOCUMENTS

| | | | |
|---|---|---|---|
| 2,755,703 | 7/1956 | Politsch et al. | 250/223 B |
| 3,328,593 | 6/1967 | Johnson et al. | 250/223 B |
| 4,017,194 | 4/1977 | Conroy et al. | 250/341 |

Primary Examiner—Davis L. Willis
Attorney, Agent, or Firm—Cushman, Darby & Cushman

[57] ABSTRACT

A method and an apparatus for measuring the wall thickness of a plastic article, particularly of a hollow rotation-symmetrical plastic article. According to the method, the wall of the plastic article is subjected to infra-red radiation and the intensity of, e.g., the continuously transmitted radiation is measured at preselected points, said intensity being a function of the wall thickness to be measured. At the same time, on one hand, the plastic article and, on the other hand, a radiation source and/or a radiation detector are set in an axial and rotational movement in relation to each other.

5 Claims, 12 Drawing Figures

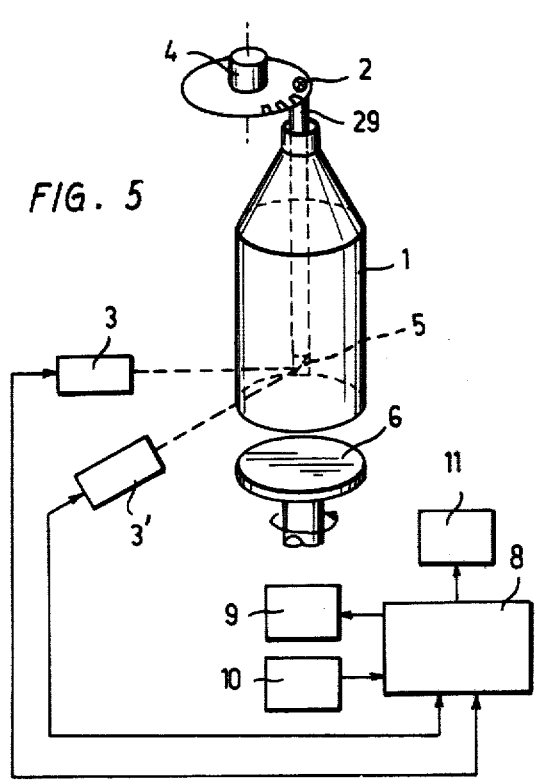
FIG. 5
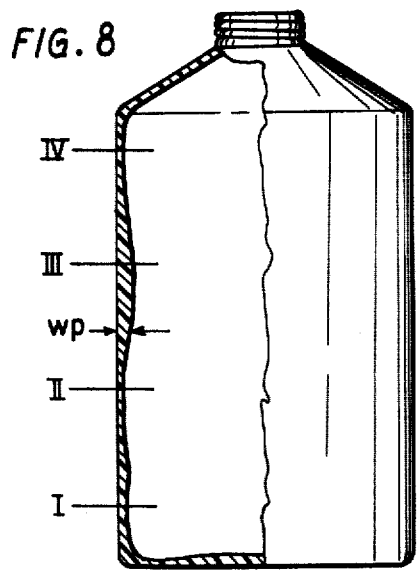
FIG. 8
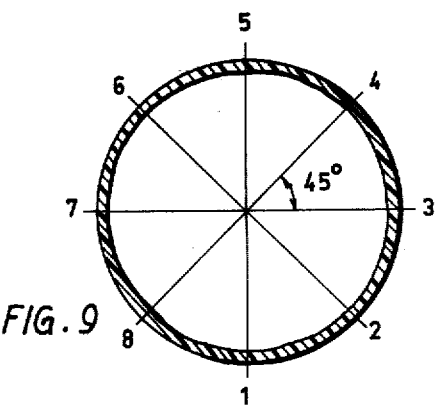
FIG. 9
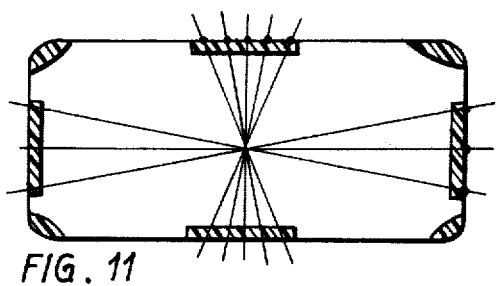
FIG. 11
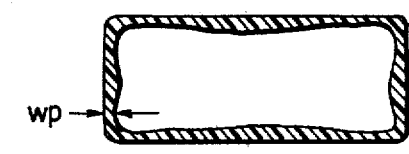
FIG. 10
| B \ S | 1. | 2. | 3. | 4. | 5. | 6. | 7. | 8. | SA |
|---|---|---|---|---|---|---|---|---|---|
| I | 101 | 96 | 101 | 102 | 107 | 104 | 102 | 81 | 99 |
| II | 107 | 101 | 106 | 106 | 109 | 93 | 104 | 108 | 104 |
| III | 109 | 103 | 108 | 107 | 108 | 110 | 108 | 110 | 107 |
| IV | 121 | 115 | 117 | 118 | 121 | 120 | 120 | 124 | 119 |
| BA | 109 | 104 | 108 | 108 | 111 | 107 | 108 | 106 | 107 |
FIG. 12

METHOD AND APPARATUS FOR MEASURING THE WALL THICKNESS IN A PLASTIC ARTICLE

This invention relates to a method for measuring the wall thickness of a plastic article, particularly of a rotation-symmetrical hollow plastic article, according to which method the wall of the plastic article is subjected to infra-red radiation.

The invention also relates to an apparatus for carrying out said method.

Measurement information is required for sorting and quality control of plastic products and for the adjustment of machines and tools. Previously, for measuring the wall thickness, destructive methods have been used and methods necessitating a firm contact to the object on test. An example of this is a measuring device employing ultra-sound.

The quality requirements for a plastic bottle are mainly directed to strength properties which are aimed at guaranteeing an undamaged condition of the package during the various handling steps. The required strength properties are best achieved by means of an appropriate choice of materials and a sufficient thickness of material.

Conventionally, the thickness of material has been controlled by means of the weight of the bottle or by means of individual measurements of the wall thickness. However, these do not indicate how the material quantity is distributed in the various parts of the bottle, which information is of a decisive importance with regard to the strength properties. Because of this disadvantage, the quality of a bottle is nowadays primarily established by means of a so-called butt load, but neither does this method indicate why a bottle is to be rejected and, consequently, it cannot be relied on when readjusting the process.

It is the object of this invention to eliminate the disadvantages in the earlier methods and to provide a method and an apparatus by means of which the wall thickness of a plastic article, in particular of a plastic bottle, can be determined without destructing the article and without touching its surface at the moment of measurement.

The invention is based on the attenuation of electromagnetic radiation and primarily infra-red radiation in the material. The attenuation depends on the properties of the material and the wavelength of the radiation.

According to one preferred embodiment of the invention, the wall thickness is measured at different levels at 32 points at equal intervals, and the information so obtained is processed in a micro-processor so that the output information will be as useful as possible.

More precisely, the method according to the invention is mainly characterized in that the intensity of the transmitted radiation is continuously measured, said intensity being a function of the wall thickness, while at the same time, on one hand, the plastic article and, on the other hand, a radiation source and/or a radiation detector are set in a mutual relative axial or rotational movement.

In a preferred embodiment the points at which the wall thickness is measured are the points defined by the intersections of a plurality of planes perpendicular to the axis of the article with a plurality of axial planes and with the wall of the article.

The invention is applicable both to laboratory-scale sample-like measurements and to sorting of products and adjustment of machines on a production line. The measurement may be carried out at points, as a measurement of the average value of a small area, or as a measurement of a continuous profile.

The invention will now be described in more detail by means of the accompanying drawings.

FIG. 5 illustrates schematically a second measuring apparatus according to the invention.

FIG. 8 shows the arrangement of the measuring levels when measuring the wall thickness in a cylindrical plastic bottle.

FIG. 9 shows the arrangement of the measuring sectors when measuring the wall thickness in a cylindrical plastic bottle.

FIG. 10 is a cross-sectional view of a rectangular bottle.

FIG. 11 shows the arrangement of the measuring sectors when measuring the wall thickness of a bottle of the type shown in FIG. 10.

FIG. 12 shows a matrix, including average value figures, comprised of the index numbers obtained on the basis of level and sector measurements.

Figure 1:
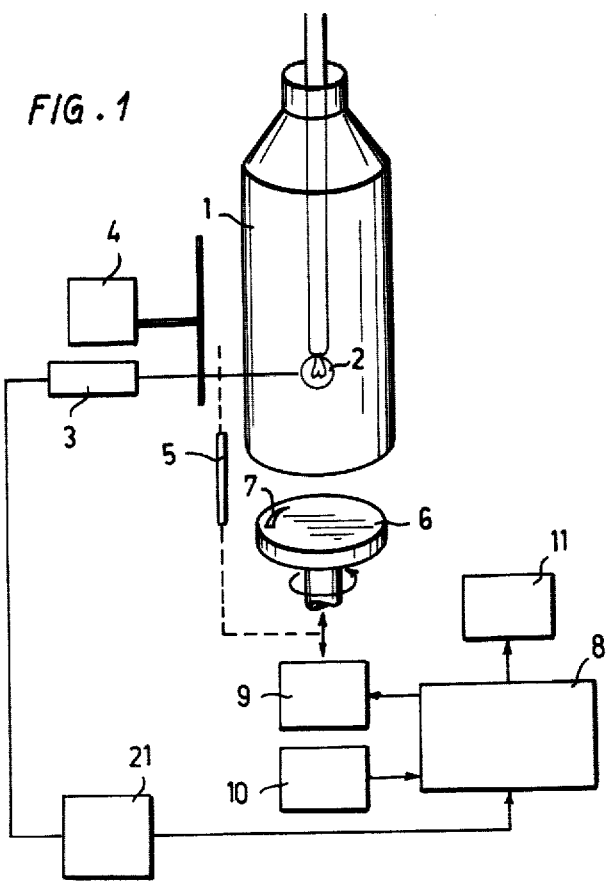
FIG. 1 illustrates schematically one measuring apparatus according to the invention.

FIG. 1 illustrates an apparatus measuring the thickness of the wall 1 of a circular plastic bottle according to the infra-red absorption principle. A radiation transmitter 2 and receiver 3 are arranged on different sides of the wall to be measured. The radiation is interrupted in order to facilitate the handling and to eliminate interferences by means of a chopper 4, and the A.C. signal obtained from a detector is amplified and filtered (21). An incandescent light bulb 2 serves as infra-red source, and an infra-red sensitive cell serves as receiver. In this embodiment, the source is disposed inside the bottle 1. The arrangement may also be such that the detector is located inside the bottle. By using a light conductor, through which the infra-red radiation passes, or a mirror reflecting the radiation, both the source and the detector can be disposed outside the bottle.

The calibration of the measuring apparatus is carried out by bringing to the measuring location a calibration sheet 5 of a known thickness and made of the material to be measured. The measurement result obtained by this sheet is stored, for example, in the memory of the measuring apparatus or in a control switch, and the result is compared to the measurement result obtained in each particular case. The calibration sheet 5 may be made, e.g., from a molten mass by pressing and by using a tool made for the purpose by means of which a sheet of a known thickness will be obtained. The calibration sheet 5 can be connected to the bottle transfer mechanism so that the sheet will always arrive at the measuring location when the bottle is absent.

During the measurement, the bottle is rotated in a carrier 6, on which it can be positioned in a specific position by utilizing a locking point 7 in the bottom of the bottle. When the position of the bottle is known, each measuring point can be localized and, accordingly, the measuring information utilized in more detail.

By employing electronics 8 known per se, it is possible to make arrangements for the processing of the measurement information, various output forms, controls of the operations of the measuring apparatus, such as controls of the transfer and rotation 9 of the bottle, and controls of the machines associated with the process. The position of the bottle is detected by position sensors 10.

The output 11 can take place, for example, merely as an accept/reject operation, by means of a picture tube, as diagrams, numerically, etc.

In the measurement, also a plurality of transmitters and/or detectors can be used to increase the measuring rate and to facilitate the gauging of more complicated wall configurations.

Figure 2:
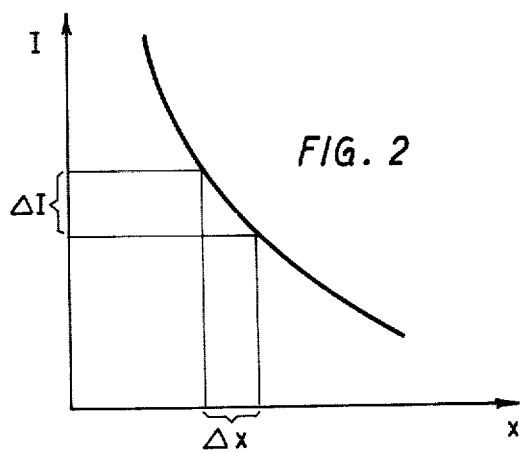
FIG. 2 illustrates graphically the intensity of radiation as a function of the thickness of material.

FIG. 2 illustrates the connection between the thickness of material and the transmitted radiation. The function is of the form $I = I_o e^{-kx}$ wherein $I$ = intensity of transmitted radiation
$I_o$ = intensity of unattenuated radiation
$k$ = material constant
$x$ = thickness of the article.

In the diagram, $\Delta I$ indicates the change in the intensity of radiation as the thickness of material changes by $\Delta x$.

Figure 3:
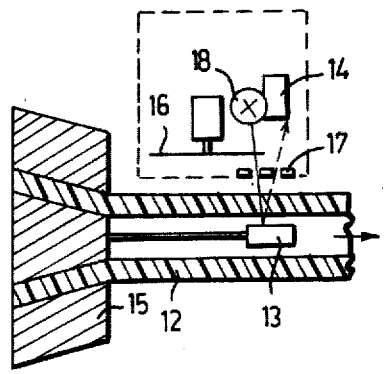
FIG. 3 illustrates partly schematically the application of infra-red measurement to the manufacture of a plastic tube.

FIG. 3 shows the principle of applying infra-red measurement to the gauging of the wall thickness of a plastic tube when manufacturing the tube.

A beam obtained from a source 18 is directed so that it passes the wall 12 of the tube, reflects back from a reflector 13 and impinges on a detector 14. The reflector is fastened to an extruder 15. The radiation is interrupted by means of a chopper 16, and the beam is by means of blinds 17 restricted so as to minimize the amount of radiation from any other source but from the reflector 13.

The part of the apparatus located outside the tube 12 can circulate along a circular path around the tube, in which case the measurement takes place along a helical line as the tube moves.

Figure 4:
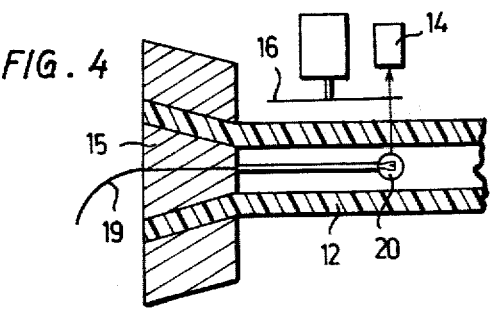
FIG. 4 illustrates partly schematically a second infra-red measuring method when manufacturing a plastic tube.

FIG. 4 illustrates a different arrangement in which a radiation source 20 is disposed within the tube 12. The power required by the source 20 can be transmitted, for example, by a conductor 19 through the extruder 15 by using batteries or by taking the power inductively from outside the tube 12. It is also possible to transmit the radiation by means of a fiber conductor into the tube, in which case the source and the detector are both located outside the tube.

FIG. 5 shows the block diagram of an apparatus according to a second embodiment. The radiation transmitter 2 and receivers 3 and 3' are located on different sides of the wall of the plastic bottle 1 to be gauged. In the intermediate space is provided a two-part mirror 5 extending inside the bottle 1 and dividing the radiation into two beams. The thickness of the straight wall is measured by one of said beams, and the thickness of the so-called "bottom angle" in the junction of the wall and the bottom is measured by the other beam.

The radiation is interrupted to facilitate the handling and to eliminate interferences by means of the chopper 4. In the receivers 3 and 3', the A.C. signal obtained from the detector is amplified and filtered to a frequency range corresponding to the gauging rate.

An incandescent light bulb serves as infra-red source, and a lead sulphite detector serves as detector. Also other types of detectors may be contemplated.

During gauging, the bottle is rotated in a holder and rotation mechanism 6, in which it can be positioned in a specific position by utilizing a locking point in the bottom of the bottle. When the position of the bottle is known, the gauging point can be localized and, accordingly, the gauging information utilized in more detail.

The operations of the device are controlled and the measurement information processed by means of a processor unit 8. The control 9 of a step motor and of the feed of the bottle, the adjustment of the amplification of the receivers, the collection 10 of coupling information and the output control 11 take place through the processor unit 8. The output 11 may take place, for example, simply as an accept/reject operation, by means of a picture tube or a printer.

Figures 6, 7:
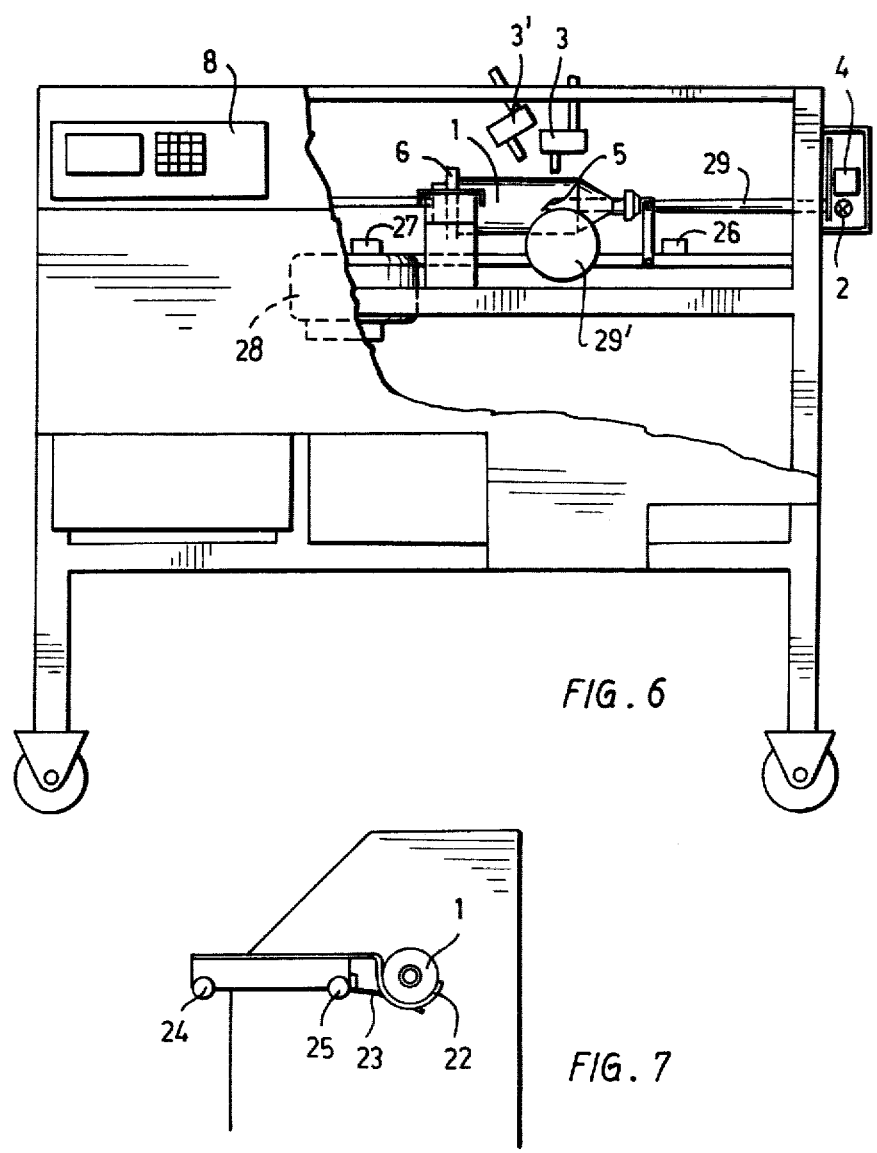
FIG. 6 illustrates one practical embodiment of the measuring apparatus according to the invention.
FIG. 7 illustrates a detail of the measuring apparatus according to FIG. 6.

When the bottle 1 to be gauged (FIGS. 6 and 7) arrives at a feed bucket 22, a bottle identifier switch 23 detects the bottle 1, and the information about the presence of the bottle is transferred to the processor unit 8. The processor unit 8 checks the situations of identifier switches 24 (bottle in front), 25 (bottle being fed), 26 (step motor behind), and 27 (step motor in front). If the switches 24 to 27 are in a position permitting the feed operation (feed bucket does not hit the axle of rotation), the bottle will be fed. When an information is obtained from the switch 25 that the feed has taken place, the step motor starts to move the bottle holder and rotation mechanism 6 in the axial direction of the bottle. The bottle 1 is first pushed into its extreme position so that the end of a mirror rod 29 is close to the bottom of the bottle. At the same time, the feed bucket 22 is retracted to take a new bottle and waits until the preceding bottle has been measured and the output has been written on the printer. The bottle 1 is rotated by means of a separate motor 28. The rotation is continuous. The bottle 1 moves in the axial direction by means of the step motor 29. The step motor is controlled from the processor unit 8 so as to stop the axial movement of the bottle 1 at required points for gauging the band. When the measurements have been carried out, the step motor returns to its original position and the bottle 1 falls off from the holder mechanism.

Between the gauging of each bottle, the amount of radiation $I_o$ coming to the detector is checked in the situation comprising only the attenuation of the air between the radiation source and the detector. The measured value $I_o$ is compared to each measurement result. This steps eliminates the effects of slow changes taking place in the measuring system, such as changes due to a decreasing lamp output, contamination, creeping of electronics, etc.

The use of a step motor offers the possibility of a rapid and exact determination of the measuring band locations. In the embodiment presented, the location of the measuring band is defined in millimeters counted from the bottom of the bottle. The keyword for the band and the distance in millimeters from the bottom of the bottle are keyed into the memory of the processor 8.

A separate detector is used for measuring the thickness of the bottom angle of the bottle. The measuring location of the bottom angle is determined by the bottle diameter because the radiation must fall obliquely on the axis of the bottle.

The calibration of the measuring apparatus for various materials is carried out by measuring the wall thickness of the bottle 1 at a specific point and by storing the measurement result obtained in the memory of the processor 8. Hereupon, a calibration measurement is carried out at the same point by means of a micrometer or a measuring clock. The measurement result given by the apparatus is converted by means of a calibration coefficient so that the result is the same as that obtained by the calibration measurement.

This procedure is based upon on such a function stored in the memory of the apparatus which exists between the thickness of material and the transmitted radiation.

The apparatus can also be used to indicate relative changes, in which case the above-mentioned calibration step is unnecessary.

In practice, the measurement takes place as follows:

(1) When the required wall profile (FIG. 8) is known 3 to 6 levels or bands are selected at which the measurements are to be carried out.

(2) For these levels, set values (wp) are set which usually are of a different magnitude at different levels.

If the cross-section of the bottle at said levels or in said bands is circular, the circumference is divided into eight sectors and, as the value for each sector, is calculated the average value of four measurement results thereto (FIG. 9).

(3) From the above measurement, a matrix is written out in which the levels selected and the number of sectors used define the size of the matrix (FIG. 12).

The measurement results are processed as a matrix (FIGS. 8, 9 and 12) comprised of four bands (I to IV) and 8 sectors (1 to 8). The members of the matrix are the ratio values formed by the ratio of the measurement result obtained and the set value multiplied by one hundred. If the measurement result is the same as the set value, the ratio number will be 100. This facilitates the interpretation of the matrix. A deviation from the set value is easy to note. The quality criteria for the bottle are formed in relation to the parts of this matrix. From the matrix, the average values BA of the bands, the average values of SA of the sectors and the average value TA of the total matrix are calculated. A permitted deviation percentage is given to the values calculated and, moreover, to the individual elements within the limits of which percentage the thickness may vary without the bottle being rejected. The bottom angle is processed separately so as to define a minimum value which is the absolute minimum for the thickness of the bottom angle.

In other words, the numerical values and average values of the matrix can be used as criteria for accepting/rejecting the bottle by means of setting the following rejection limits (a) for individual matrix values (e.g., ±20%)

(b) for the average values of the vertical and horizontal lines (±10%)

(c) for the average value of the total matrix (+5%).

The measurement results can also be used by calculating the average value matrices for a required number, whereby a picture of the average deviations in the entire production is obtained. Such an information is of advantage when supervising the adjustments of machines and, on the other hand, when observing changes occurring in the manufacturing process in the course of time.

The average value readings can also be controlled by calculating their average values up to a quantity of 999 from successive bottles. On the basis of this, changes in thickness occurring during a longer period may be determined.

Changes in the wall location between the radiation source 2 and the detector and in the angle of incidence of radiation will result in changes in the measurement results. This circumstance prevents the measurement of non-circular bottles without correcting factors. For this reason, a solution has been developed in which the measurement of a non-circular bottle (FIGS. 10 and 11) is by means of coefficients converted to be carried out in the same way as the measurement of circular bottles. In other words, incorrect intensity values due to non-circularity are converted to correct ones by means of a coefficient matrix for each particular type of bottle. The coefficient matrix can be used in programming by storing the matrix in the memory of the apparatus. In slow apparatus applications, the matrix can also be used manually.

If the cross-section of the bottle is not circular, the measurement results are thus grouped so as to realize an appropriate inspection. For example, in the case of a rectangular or oval cross-section, the solution according to FIG. 1 is preferred.

In case of deviating configurations, it is also possible to construct for each particular bottle type a disc controlling the measuring impulses instead of the present 32-index disc and, in this way, the measuring signals are applied to the required points on the circumference.

Variations in material and colour are taken into account by calibrating the measuring apparatus by means of the first product to measured such that the value of the first location in the matrix is separately measured by means of a measuring clock and the thickness value (mm) obtained is fed through the keyboard to the processor.

A variation in the configuration includes two separate components resulting in an error in the measurement results.

(a) the surface to be measured is not at right angles to the radiation (b) the distance of the surface to be measured during the rotational movement changes in relation to the detector and the radiation source.

In both cases, the measurement error due to the variation is corrected experimentally by the correction coefficient obtained. The correction coefficients can be taken into account when setting the set values or by constructing a separate correction matrix in the software.

The method can also be employed in the inspection of so-called critical objects, in which case the measurements are carried out at the critical point so defined and the measurement value obtained is compared to an acceptable minimum value. If the measurement value is less than the minimum value, the product will be rejected and, in the opposite case, accepted.

It should be mentioned that the measurement of the bottom angle involves the use of a special disc in the synchronization of the radiation when measuring bottles the cross-section whereof differs from a circular one.

What we claim are:

1. A method for measuring the wall thickness of a rotation-symmetrical hollow plastic article having a side wall and a bottom joined thereto comprising positioning a source of penetrating radiation, two radiation detectors on the same side of the wall and positioning a two-part radiation reflector on the opposite side of the wall, one of the reflector parts being arranged to receive radiation from the source and to reflect it through the wall of the article to one of the detectors and the other reflector part being arranged to receive radiation from the source and to reflect it in a direction at an angle to the direction of the first-mentioned reflected radiation; effecting intermittent relative rotation and relative axial movement between the article and at least one of said source and said detector; measuring the intensity of the radiation passing through the wall of the article at a plurality of circumferentially spaced apart discrete points at each of a plurality of locations along the axis of the article; and, at least one axial position of the article, passing the radiation from said other reflector part through the junction area of the side wall of the article with the bottom; and recording a thickness measurement for each of said points.

2. A method as in claim 1 wherein said points are the points of intersection of a plurality of planes perpendicular to the axis of the article with a plurality of axial planes and with the wall of the article.

3. A method as in claim 2 wherein the article is rotated about its axis stepwise.

4. A method as in claim 1 wherein the radiation is infrared radiation.

5. Apparatus for measuring the wall thickness of a rotation-symmetrical hollow plastic article having a side wall and a bottom wall, said apparatus comprising: a source of penetrating radiation; first and second detectors for the penetrating radiation located on the same side of the wall which is to be measured; a radiation reflector located on the opposite side of the wall which is to be measured, said reflector including a two-part mirror dividing the radiation from the source into two beams the first of which is directed to pass through the side wall of the article and the second of which is directed at an angle to the first beam; means for effecting stepwise relative axial movement between the article and the source and the detectors such that in at least one axial position of the article the second reflected beam passes through the junction area of the side wall with the bottom; and means for effecting stepwise relative rotational movement about the axis of the article between the article and the source and the detectors.

* * * * *